United States Patent [19]

Koch et al.

[11] Patent Number: 4,741,848

[45] Date of Patent: May 3, 1988

[54] BORON-CONTAINING COMPOSITIONS, AND LUBRICANTS AND FUELS CONTAINING SAME

[75] Inventors: Frederick W. Koch, Willoughby Hills; Joseph W. Pialet; Daniel E. Barrer, both of Euclid; Calvin W. Schroeck, Eastlake, all of Ohio

[73] Assignee: The Lubrizol Corporation, Wickliffe, Ohio

[21] Appl. No.: 839,754

[22] Filed: Mar. 13, 1986

[51] Int. Cl.$^4$ .................. C10M 129/00; C10M 133/16
[52] U.S. Cl. ..................... 252/49.6; 252/51.5 A; 548/405; 564/170; 564/176; 564/177; 564/201
[58] Field of Search ..................... 252/51.5 A, 49.6; 564/201, 170, 177, 176; 548/405

[56] References Cited

U.S. PATENT DOCUMENTS

| | | | |
|---|---|---|---|
| 3,183,069 | 5/1965 | Udelhofen et al. | 252/51.5 A |
| 4,237,022 | 12/1980 | Barrer | 252/51.5 A |
| 4,255,586 | 3/1981 | Harrington et al. | 556/402 |
| 4,353,807 | 10/1982 | Braid | 252/49.6 |
| 4,392,973 | 7/1983 | Moore et al. | 252/78.1 |
| 4,394,277 | 7/1983 | Small, Jr. | 252/32.7 E |
| 4,401,580 | 8/1983 | Frost | 252/25 |
| 4,406,802 | 9/1983 | Harodysky et al. | 252/49.6 |
| 4,440,656 | 4/1984 | Horodysky | 252/49.6 |
| 4,446,038 | 5/1984 | Schlicht et al. | 252/51.5 A |
| 4,459,215 | 7/1984 | Solentine | 252/32.5 |
| 4,512,903 | 4/1985 | Schlicht et al. | 252/51.5 A |
| 4,557,846 | 12/1985 | Wisotsky | 252/51.5 A |
| 4,594,171 | 6/1986 | Horodysky et al. | 252/49.6 |

Primary Examiner—William R. Dixon, Jr.
Assistant Examiner—Margaret B. Medley
Attorney, Agent, or Firm—James L. Cordek; Denis A. Polyn; Joseph P. Fischer

[57] ABSTRACT

A method of preparing boron-containing compositions is described which comprises reacting at least one hydroxy-substituted ester, amide or imide with a boron compound. Such boron-containing compositions are useful in lubricating oils and provide the lubricating oils with anti-wear and/or friction-reducing properties. The boron-containing compositions also are useful in fuel compositions.

34 Claims, No Drawings

BORON-CONTAINING COMPOSITIONS, AND LUBRICANTS AND FUELS CONTAINING SAME

BACKGROUND OF THE INVENTION

The use of various boron-containing compounds as extreme pressure and anti-wear additives for lubricating oils has been suggested in the prior art.

There continues to be a need for lubricants of sufficient lubricity to provide lubricating between the bearing surfaces of moving metal components where the bearing surfaces are subjected to large forces at the point of contact. These forces and the accompanying friction result in the generation of heat which elevates the metal temperatures. If the pressure is sufficiently high and the relative motion between surfaces sufficient, very high metal temperatures can result. Thus, in extreme cases, the contacting metal surfaces may actually weld one to the other. With less extremes of pressure, inadequate lubrication between surfaces is manifested in accelerated wear, scuffing, etc.

In addition to anti-wear and extreme pressure properties, lubricants for use in limited slip differentials require unusual frictional properties. Limited slip differentials are unlike conventional differentials in that they have the ability to move a vehicle when only one wheel has traction. This advantage is accomplished through an internal clutch that restricts conventional differential action and tends to make the left and right rear axle shafts turn as one. There are a variety of clutch arrangements employed to accomplish this result but most rely on the force of friction to restrict the free turning of the axle shaft. Since the clutches are continuously contacted by the differential lubricant, the restricting force depends on the coefficient of friction imparted to the engaging parts by said lubricant. The coefficient of friction must be compromised. On the other hand, it must be high enough to allow the clutch plates to seize, thus allowing the vehicle to move in instances when one rear wheel has low traction and, on the other hand, it must be sufficiently low to allow the clutch plates to slip and accomodate conventional differential action such as occurs when the vehicle turns corners. The ability of a lubricant to impart a coefficient of friction within this fairly wide effective range is referred to as effectiveness.

Another important aspect of frictional properties relates to the chatter or noise caused by the differential action of clutches. Chatter is generated by a stick-slip action of the engaging parts of the clutches. Differential manufacturers have found that stick-slip is primarily the result of the static coefficient of friction being greater than the dynamic coefficient of friction. That is, when the ratio of the static coefficient of friction to the dynamic coefficient of friction is greater than one.

Many diverse additives for enhancing anti-wear, extreme pressure and friction modifying properties are well known in the prior art. Examples of such additives are chlorinated waxes, alkyl polysulfides, alkyl phosphites, alkaryl phosphates, metal dithiophosphates, sulfurized sperm oil, sulfurized olefins, alkali metal borates, and the like. However, a need still exists for materials which can provide these properties and combinations of these properties.

U.S. Pat. No. 4,512,903 describes the preparation of amides from mono- or polyhydroxy-substituted aliphatic monocarboxylic acids and primary or secondary amines. The amides are reported to be useful as friction reducing agents when incorporated into fuels or lubricants. U.S. Pat. No. 4,406,802 describes various borated additive compositions which are useful in lubricating compositions as multi-functional additive compounds having friction-reducing and oxidation and corrosion-inhibiting characteristics. In general, the boron-containing compounds are borates of mixed alcohols, amides, amines, and hydroxy esters, ethoxylated amines and ethoxylated amides and mixtures thereof.

SUMMARY OF THE INVENTION

This invention is directed to the preparation of novel boron-containing compositions and to the use of such compositions in lubricants and fuels. The boron-containing compositions of the present invention are prepared by the process which comprises reacting (A) at least one hydroxy-substituted ester, amide, or imide of the formula

wherein R is a divalent hydrocarbyl group, X is —OR' or —NR'R", wherein R' is a hydrocarbyl group and R" is hydrogen or a hydrocarbyl group, Y is OH or X, m is zero to 2, or X and one Y taken together represent a single NR' group forming a cyclic imide, and n is an integer from 1 to 10 provided that only one free hydroxyl group is attached per carbon atom of the hydrocarbyl group R, with (B) a boron compound selected from the group consisting of boric acid, boron trioxide, boron halides, boron amides and boron esters.

In addition to the method of preparing such boron-containing compositions and the compositions per se, the present invention also relates to the use of such compositions in lubricant and fuel compositions. The boron-containing compositions of the invention are incorporated into lubricating compositions to improve fuel economy, and reduce friction and wear.

DESCRIPTION OF THE PREFERRED EMBODIMENTS

The boron-containing compositions of the present invention may be prepared by reacting (A) at least one hydroxy-substituted ester, amide or imide with (B) a boron compound.

Reactant (A):

Reactant (A) may be at least one hydroxy-substituted ester, amide, or imide of the formula

wherein R is a divalent hydrocarbyl group, X is —OR' or —NR'R", wherein R' is a hydrocarbyl group and R" is hydrogen or a hydrocarbyl group, Y is OH or X, m is zero to 2, or X and one Y taken together represent a single NR' group forming a cyclic imide, and n is an integer from 1 to 10 provided that only one free hydroxyl group is attached per carbon atom of the hydrocarbyl group R. As can be noted, the ester, amide or imide may be derived from a mono-, di-, or tricarboxylic acid.

In the above Formula I, R is a divalent hydrocarbyl group including alkylene, alkenylene, alkynylene, arylene or alkarylene groups containing generally from about 1 to 10 carbon atoms. The hydrocarbyl group R may be aliphatic, alicyclic, aromatic, aliphatic- and alicyclic-substituted aromatic, aromatic-substituted aliphatic, etc. Preferably, the hydrocarbyl group R is an alkylene group containing from 1 to about 5 carbon atoms, and n is from 1 to about 5. Even more generally, R will contain from 1 to about 3 carbon atoms, and n will be from 1 to 3. The hydrocarbyl groups R' and R'' may contain up to about 150 carbon atoms, and preferably will contain from about 4 to about 30 carbon atoms.

In one embodiment, reactant (A) is a hydroxy-substituted amide having the structure

$(HO)_n$—R—$(C(O)NR'R'')_m$      (II)

wherein m, n, R, R' and R'' are as defined above with respect to Formula I.

In another embodiment, a reactant (A) is a hydroxy-substituted imide having the structure

(III)

wherein n, R and R' are as defined above with respect to Formula I.

In yet another embodiment, the reactant (A) is a hydroxy-substituted ester of the formula

(IV)

wherein m, n, R and R' are as defined above with respect to Formula I, and Z is —OH ro —OR'. Accordingly, the hydroxy-substituted esters of Formula IV may be monoesters, di- or triesters and/or mixed acid esters.

The hydroxy-substituted esters useful as reactant (A) in the present invention may be prepared by reacting (A-1) at least one hydroxy-substituted carboxylic acid, acid anhydride, ester or halide, or a lactone with (A-2) an alcohol or mixture of alcohols. The amides and/or imides useful as reactant (A) can be prepared by the reaction of (A-1) a hydroxy-substituted carboxylic acid, acid anhydride, ester or halide, or a lactone with (A-2) at least one primary or secondary hydrocarbyl amine.

The hydroxy-substituted carboxylic acids, esters, and halides useful in the preparation of reactant (A) may be represented by the formulae

$(HO)_nRC(O)Y'$, or      (V)

(VI)

wherein R is a divalent hydrocarbyl group, m is 0 to 2, n is an integer from 1 to 10 provided that only one free hydroxyl group is attached per carbon atom of the hydrocarbyl group R, and Y' is —OH— a halogen, or OR''' wherein R''' is a lower alkyl group. Generally, reactant (A-1) will be a hydroxy-substituted mono- or polycarboxylic acid (i.e., Y' is OH). When reactant (A-1) is an ester, one or more of the Y' groups is OR''' wherein R''' is a lower alkyl group containing from 1 to about 4 or 5 carbon atoms. Preferably, the alkyl group R''' is a methyl group or an ethyl group.

Suitable hydroxy-substituted monocarboxylic acids include hydroxyacetic acid, glycolic acid, mandelic acid, 2-hydroxypropionic acid, 3-hydroxypropionic acid, 2-hydroxybutyric acid, 3-hydroxybutyric acid, 4-hydroxybutyric acid, and 2,2-bis-$(HOCH_2)_2$ propionic acid.

The hydroxy-substituted monocarboxylic acids also may be aromatic hydroxy-carboxylic acids such as salicylic acid, 3-chloro-2-hydroxy-benzoic acid, 3-methyl-2-hydroxy-benzoic acid, beta or gamma-resorcylic acid, 2-hydroxy-1-naphthoic acid, 1-hydroxy-2-naphthoic acid, etc.

Examples of hydroxy-substituted polycarboxylic acids useful in the method of the present invention include tartronic acid, tartaric acid, malic acid, dihydroxy-maleic acid, citric acid, etc. The corresponding anhydrides also may be used.

The hydroxy-substituted amides useful as reactant (A) in the present invention also may be prepared by the reaction of a lactone of the formula

(VII)

wherein R is a divalent hydrocarbyl group, with at least one primary or secondary hydrocarbyl amine. Generally, R will be a divalent hydrocarbyl group containing up to about 5 to 6 carbon atoms. Examples of suitable lactones include gamma-butyrolactone, valerolactone and caprolactone.

The amines which are reacted with the abovedescribed hydroxy-substituted carboxylic acids, acid anhydride, esters or halides, or the lactones of Formula VII, are primary or secondary hydrocarbyl amines having the general formula

R'R''NH      (VIII)

wherein R' is a hydrocarbyl group and R'' is hydrogen or a hydrocarbyl group. Generally, the hydrocarbyl group R' and R'' will contain up to about 150 carbon atoms and will more often be aliphatic hydrocarbyl groups containing from about 4 to about 30 carbon atoms.

In one preferred embodiment, the hydrocarbyl amines which are useful in preparing the amides and imides of the present invention are primary hydrocarbyl amines containing from about 4 to about 30 carbon atoms in the hydrocarbyl group, and more preferably from about 8 to about 20 carbon atoms in the hydrocarbyl group. The hydrocarbyl group may be saturated or unsaturated. Representative examples of primary saturated amines are those known as aliphatic primary fatty amines and commercially known as "Armeen" primary amines (products available from Armak Chemicals, Chicago, Ill.). Typical fatty amines include alkyl amines such as N-hexylamine, N-octylamine, N-decylamine, N-dodecylamine, N-tetradecylamine, N-pentadecylamine, N-hexadecylamine, N-octadecylamine (stearyl amine), etc. These Armeen primary amines are available in both distilled and technical grades. While the distilled grade will provide a purer reaction product, the desirable amides and imides will form in reactions with the amines of technical grade.

Primary amines in which the hydrocarbon chain comprises olefinic unsaturation also are quite useful. Thus, the R' and R" groups may contain one or more olefinic unsaturation depending on the length of the chain, usually no more than one double bond per 10 carbon atoms. Representative amines are dodecenylamine, myristoleyamine, palmitoleylamine, oleylamine and linoleylamine. Such unsaturated amines also are available under the Armeen tradename.

Also suitable are mixed fatty amines such as Armak's Armeen-C, Armeen-O, Armeen-OL, Armeen-T, Armeen-HT, Armeen S and Armeen SD. Secondary amines include dialkylamines having two of the above alkyl groups including such commercial fatty secondary amines as Armeen 2C and Armeen HT, and also mixed dialkylamines where R' is a fatty amine and R" may be a lower alkyl group (1–9 carbon atoms) such as methyl, ethyl, n-propyl, i-propyl, butyl, etc., or R" may be an alkyl group bearing other non-reactive or polar substituents (CN, alkyl, carbalkoxy, amide, ether, thioether, halo, sulfoxide, sulfone) such that the essentially hydrocarbon character of the radical is not destroyed. The fatty polyamine diamines include mono- or dialkyl, symmetrical or asymmetrical ethylene diamines, propane diamines (1,2, or 1,3), and polyamine analogs of the above. Suitable commercial fatty polyamines are "Duomeen C" (N-coco-1,3-diaminopropane), "Duomeen S" (N-soya-1,3-diaminopropane), "Duomeen T" (N-tallow-1,3-diaminopropane), or "Duomeen O" (N-oleyl-1,3-diaminopropane). "Duomeens" are commercially available diamines described in Product Data Bulletin No. 7-10R1 of Armak Chemical Co., Chicago, Ill.).

Other primary amines useful in the preparation of the amides and imides are the primary ether amines R"OR'NH$_2$ wherein R' is a divalent alkylene group having 2 to 6 carbon atoms and R" is a hydrocarbyl group of about 5 to about 150 carbon atoms. These primary ether amines are generally prepared by the reaction of an alcohol R"OH with an unsaturated nitrile. The R" group of the alcohol can be a hydrocarbon-based group having up to about 150 carbon atoms. Typically, and for efficiency and economy, the alcohol is a linear or branched aliphatic alcohol with R" having up to about 50 carbon atoms, preferably up to 26 carbon atoms and most preferably R" has from 6 to 20 carbon atoms. The nitrile reactant can have from 2 to 6 carbon atoms with acrylonitrile being most preferred. Ether amines are known commercial products which are available under the name SURFAM ™ produced and marketed by Mars Chemical Company, Atlanta, Ga. Typical of such amines are those having from about 150 to about 400 molecular weight. Preferred etheramines are exemplified by those identified as SURFAM P14AB (branched C$_{14}$), SURFAM P16A (linear C$_{16}$), SURFAM P17AB (branched C$_{17}$). The carbon chain lengths (i.e., C$_{14}$, etc.) of the SURFAMS described above and used hereinafter are approximate and include the oxygen ether linkage. For example, a C$_{14}$ SURFAM would have the following general formula $C_{10}H_{21}OC_3H_6NH_2$ The preparation of the hydroxy-substituted amides and imides utilized in the preparation of the boron-containing compositions of the present invention is effected by techniques well known in the art. The amides generally will be prepared by reacting approximately equal amounts of the acid, acid anhydride, acid ester or acid halide with one or more of the primary or secondary amines described above. When the hydroxy-substituted carboxylic acid (or derivative) is a polycarboxylic acid (or derivative), and the amine is a primary amine, the reaction product may be the corresponding amide, imide or a mixture of amide and imide depending on the reaction conditions. Generally, the reaction products will be primarily an imide (Formula III).

In general, the reaction of the hydroxy-substitued carboxylic acid (or derivative) with the primary or secondary amine is conducted at atmospheric, superatmospheric or sub-atmospheric pressure at temperatures ranging from about room temperature to about decomposition temperature of the mixture or of any products formed from the reaction mixture. Preferably, the reaction is carried out at atmospheric pressure and at temperatures below about 200° C. A preferred range of temperatures at atmospheric pressure is from about 60° to about 180° C. Generally, the reaction is conducted until water evolution ceases.

The preparation of the hydroxy-substituted carboxylic acid amides and imides can be carried out conveniently in solvents, particularly those which can withstand relatively high reaction temperatures and which are inert toward the reactants and the desired product. Various hydrocarbon solvents are particularly useful, and these include, for example, toluene, xylene, ethyl benzene, benzene, and mineral oils. More volatile solvents such as toluene and xylene are preferred where it is desired to remove the solvent by conventional techniques at the end of the reaction. Mineral oils are desirable as solvents for the reaction when the oil does not have to be removed from the reaction product such as when the product is to be used as additives for lubricants. Alternatively, in some instances, no solvent at all is used.

Reactant (A) also may be a hydroxy-substituted ester of the formula

(IV)

wherein R is a divalent hydrocarbyl group, R' is a hydrocarbyl group, m is 0 to 2, n is an integer of from 1 to about 10 provided that only one free hydroxyl group is attached per carbon atom of the hydrocarbyl group R, and Z is —OH or —OR'. The definitions and descriptions of R, R', m and n given above with respect to the compounds represented by Formulae I and II are applicable to the same terms as utilized in hydroxy-substituted esters represented by Formula IV. Accordingly, for example, R' is a hydrocarbyl group containing up to about 150 carbon atoms and more generally from 4 to about 30 carbon atoms, and R is preferably an alkylene, alkenylene, alkynylene, arylene or alkarylene group containing from 1 to about 10 carbon atoms. When m is 1 or 2, the hydroxy-substituted ester represented by Formula IV may be a di- or triester or a mixed esteracid.

The esters represented by Formula IV may be obtained by the reaction of hydroxy-substituted acids with alcohols represented by the formula R'OH. Alternatively, the derivatives of the acids such as anhydrides, halides, or esters derived from lower alkanols can be reacted with the alcohols of the formula R'OH to form the desired higher molecular weight esters. The various acids and acid derivatives described above with respect to the formation of the amide products (Formula II) can be utilized in the preparation of the corresponding hydroxy-substituted esters (Formula IV) which are useful in the present invention.

The alcohols R'OH which can be utilized to provide the desired esters are well known, and include, for example, monohydric as well as polyhydric alcohols, and primary as well as secondary alcohols as well as mixtures of these alcohols.

The preferred monohydric alcohols are primary aliphatic alcohols, especially aliphatic hydrocarbon alcohols such as alkenols and alkanols of from about 4 to about 30 carbon atoms, and preferably from about 8 to about 30 carbon atoms. Mixtures of alcohols can be utilized provided that the total number of carbon atoms in the two R' groups is at least about 8. More preferably, each R' group is derived from a monohydric alcohol containing at least 8 carbon atoms. Accordingly, examples of the preferred monohydric alcohols from which the R' group is derived include 1-octanol, 1-decanol, 1-dodecanol, 1-tetradecanol, 1-hexadecanol, 1-octadecanol, oleyl alcohol, linoleyl alcohol, linolenyl alcohol, phytol, myricyl alcohol, lauryl alcohol, myristyl alcohol, cetyl alcohol, stearyl alcohol and behenyl alcohol.

Of course, commercial alcohols (mixtures) are contemplated herein, and these commercial alcohols may comprise minor amounts of alcohols which, although not specified herein, do not detract from the major purposes of this invention. Higher synthetic monohydric alcohols of the type formed by the Oxo process (e.g., 2-ethylhexyl), the aldol condensation, or by organoaluminumcatalyzed oligomerization of the alpha-olefins (especially ethylene), followed by oxidation, also are useful.

Examples of some preferred monohydric alcohols and alcohol mixtures suitable for forming the esters useful in the compositions of the invention include commercially available "Alfol" alcohols marketed by Continental Oil Corporation. Alfol 810 is a mixture containing alcohols consisting essentially of straight chain, primary alcohols having from 8 to 10 carbon atoms. Alfol 12 is a mixture comprising mostly $C_{12}$ fatty alcohols. Alfol 1218 is a mixture of synthetic primary straight chain alcohols having 12 to 18 carbon atoms. The Alfol 20+ alcohols are mixtures of $C_{18}$–$C_{28}$ primary alcohols having mostly, on an alcohol basis, $C_{20}$ alcohols as determined by GLC (gas-liquidchromatography). The Alfol 22+ alcohols are $C_{18}$–$C_{28}$ primary alcohols having mostly, on an alcohol basis, $C_{22}$ alcohols. These Alfol alcohols can contain a fairly large percentage (up to 40% by weight) of paraffinic compounds which can be removed before the esterification reaction if desired.

Another example of a commercially available alcohol mixture is Adol 60 which comprises about 75% by weight of a straight chain $C_{22}$ primary alcohol, about 15% of a $C_{20}$ primary alcohol and about 8% of $C_{18}$ and $C_{24}$ alcohols. Adol 320 comprises predominantly oleyl alcohol. The Adol alcohols are marketed by Ashland Chemical.

A variety of mixtures of monohydric fatty alcohols derived from naturally occurring triglycerides and ranging in chain length of from $C_8$ to $C_{18}$ are available from Procter & Gamble Company. These mixtures contain various amounts of fatty alcohols containing mainly 12, 14, 16, or 18 carbon atoms. For example, CO-1214 is a fatty alcohol mixture containing 0.5% of $C_{10}$ alcohol, 66.0% of $C_{12}$ alcohol, 26.0% of $C_{14}$ alcohol and 6.5% of $C_{16}$ alcohol.

Another group of commercially available mixtures include the "Neodol" products available from Shell Chemical Co. For example, Neodol 23 is a mixture of $C_{12}$ and $C_{13}$ alcohols; Neodol 25 is a mixture of $C_{12}$ and $C_{15}$ alcohols; and Neodol 45 is a mixture of $C_{14}$ and $C_{15}$ linear alcohols. Neodol 91 is a mixture of $C_9$, $C_{10}$ and $C_{11}$ alcohols.

Fatty vicinal diols also are useful and these include those available from Ashland Oil under the general trade designation Adol 114 and Adol 158. The former is derived from a straight chain alpha olefin fraction of $C_{11}$–$C_{14}$, and the latter is derived from a $C_{15}$–$C_{18}$ fraction.

Examples of branched chain monohydric alcohols suitable for forming the esters useful in the present invention include, for example, commercial tridecyl alcohol corresponding in large part substantially to the formula

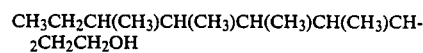

prepared by the Oxo process and which is available from Exxon Corporation, hexadecyl alcohol prepared by the Oxo process, 12-methylpentadecyl alcohol, 6-methyldecyl alcohol, 8-ethyltetradecyl alcohol, 5,6-dipropyldecyl alcohol as well as mixtures of these alcohols. Branched chain alcohols of from 12 to 14 carbon atoms with one or more methyl branches are the more preferred.

The hydroxy-substituted esters (IV) can be obtained by esterification of the corresponding acid or acid derivative such as lower alkyl ester, halide or anhydride, with one or more of the above described alcohols under conditions which are typical for effecting esterification. Such conditions include, for example, a temperature of up to the reflux temperature of the mixture provided that the temperature is maintained at a level below the decomposition of the reaction mixture or any products thereof. Water (or volatile halides or esters) normally is removed as the esterification proceeds. These conditions optionally may include the use of an excess amount of alcohol over the stoichiometric requirements for complete esterification with the alcohols in order to facilitate the esterification reaction.

Generally, the esterification reaction is conducted in a substantially inert, normally liquid, organic solvent or diluent such as mineral oil, toluene, benzene, xylene and the like. Esterification catalysts may be included in the mixture, and these catalysts include acid-form cationic exchange resins, toluene-sulfonic acid, sulfuric acid, aluminum chloride, boron trifluoride-triethylamine, methanesulfonic acid, hydrochloric acid, ammonium sulfate, phosphoric acid, sodium methoxide, alkanoic acids such as acetic, propionic and butyric acids, etc. The amount of catalyst is typically less than about 0.5 mole, and most often about 0.01 to about 0.3 mole per mole of reagent (A-1).

The following examples illustrate the preparation of reactant (A) useful in the preparation of the boron-containing compositions of the present invention. Unless otherwise indicated in the following examples, and elsewhere in the specification and claims, all parts and percentages are by weight and all temperatures are in degrees centigrade.

EXAMPLE 1-A

A mixture of 500 parts of CO-1214 (a fatty alcohol available from Procter & Gamble Company containing about 0.5% of $C_{10}$ alcohol, 66.0% of $C_{12}$ alcohol, 26.0% of $C_{14}$ alcohol, and 6.5% of $C_{16}$ alcohol), 100 parts of toluene and 2 parts of paratoluenesulfonic acid is prepared and heated to a temperature of about 90° C. whereupon 271.5 parts of 70% aqueous solution of hydroxyacetic acid are added slowly in several parts while water is azeotroped from the mixture. The mixture then is heated to the reflux temperature and additional water is removed while maintaining an atomsphere of nitrogen. Sodium bicarbonate is added to neutralize the catalyst, the reaction product is filtered through a filter aid and the filtrate is stripped to remove volatile materials. The residue is the desired product.

EXAMPLE 2-A

A mixture of 300 parts (67% solution) of hydroxyacetic acid, 695 parts of oleyl alcohol, 2 parts of paratoluenesulfonic acid and about 400 parts of benzene is prepared. The mixture is stirred and heated to an elevated temperature while removing water. The heating was maintained for a period of about 12 hours while a total of 135 parts of water is removed. The solvent then is removed under vacuum leaving a darkbrown residue which is the desired product.

EXAMPLE 3-A

A mixture of 340 parts of hydroxyacetic acid (67% aqueous solution) 555 parts of Alfol 12, 25 parts of Amberlyst 15 and 200 parts of benzene is prepared and heated to about 90° C. A benzene-water azeotrope is removed over a period of 16 hours. The residue is the desired product.

EXAMPLE 4-A

A mixture of 340 parts of hydroxyacetic acid (67% in water), 591 parts of FOH-1214, 30 parts of Amberlyst 15 and 250 parts of benzene is prepared and heated at the reflux temperature while removing water. Benzene is then removed, and the residue is the desired product.

EXAMPLE 5-A

A mixture of 600 parts of toluene and 1897 parts of oleylamine (Armeen O) is prepared and heated to the reflux temperature whereupon 760.2 parts of hydroxyacetic acid (70% in water) is added dropwise. Water is removed as an azeotrope, and the residue is stripped of volatile materials under partial vacuum and filtered. The filtrate is the desired amide.

EXAMPLE 6-A

A mixture of 588 parts of Armeen C (mixed primary fatty amines primarily cocoamine) and 150 parts of toluene is prepared and heated to a temperature of about 90° C. whereupon 317.5 parts of hydroxyacetic acid (67% in water) are added dropwise under a nitrogen sweep. Water is removed as an azeotrope and the residue is stripped under mild vacuum. The stripped residue is the desired product containing 5.41% nitrogen (theory, 5.22%).

EXAMPLE 7-A

A mixture of 228 parts of caprolactone and 540 parts of oleylamine (Armeen O) is prepared and heated to a temperature of about 110° C. thereafter to a temperature of about 140° C. over a period of two days. On cooling, the desired amide is recovered containing 3.65% nitrogen (theory, 3.65%).

EXAMPLE 8-A

A mixture of 907 parts of hydroxyacetic acid (67% in water), 1152 parts of Alfol 810 (a mixture of essentially straight chain, primary alcohols having from 8 to 10 carbom atoms) and 50 parts of Amberlyst-15 is prepared and heated to a temprature of about 110° C. whereupon water is removed. After about 400 parts of water is recovered, the residue is filtered to give a yellow fluid oil which is the desired product.

EXAMPLE 9-A

A mixture of 1540 parts of di-cocoamine (Armeen 2C), 300 parts of tartaric acid and 2 parts of paratoluenesulfonic acid is prepared and heated to about 90° C. and water is removed by distillation. After all of the water is removed, the temperature of the reaction mixture is raised to about 200° C. and filtered through a filter aid. The filtrate is the desired product containing 2.99% nitrogen.

EXAMPLE 10-A

A mixture of 150 parts (1.0 mole) of tartaric acid, 261 parts (1.0 mole) of oleylamine (Armeen O), and 350 parts of toluene is stirred and heated to 90°–100° C. The viscous mixture then is heated to 140°–170° C. while removing toluene and water. The residue is filtered through a filter aid, and the filtrate is the desired product containing 3.4% nitrogen (theory, 3.7).

EXAMPLE 11-A

A mixture of 540 parts of oleylamine and 200 parts of toluene is prepared, and 180 parts of lactic acid is added dropwise at a temperature of about 80°–100° C. while maintaining a nitrogen atmosphere. The reaction mixture is heated to reflux, and water is removed. The residue is stripped under a vacuum and filtered through filter aid. The filtrate is the desired product containing 4.13% nitrogen (theory, 4.09%).

EXAMPLE 12-A

A mixture of 548 parts (2 moles) of Armeen 18 (octadecylamine) and 200 parts of xylene is heated until the mixture is fluid whereupon 180 parts (2 moles) of lactic acid are added dropwise. When the addition of the lactic acid is completed, the mixture is heated at reflux (at about 140° C.) while blowing with nitrogen, and the water is removed. The residue is the desired product.

EXAMPLE 13-A

A mixture of 680 parts (2 moles) of Duomeen T (N-tallow-1,3-diaminopropane) and 200 parts of xylene is heated until fluid whereupon 360 parts (4 moles) of lactic acid are added in small increments. The reaction mixture is heated at reflux (about 140° C.) while stirring and blowing with nitrogen. Water is removed, and after all the water is removed, the mixture is stripped to a temperature of 195° C. at 7 mm Hg. The residue is filtered, and the filtrate is the desired product.

EXAMPLE 14-A

A mixture of 416 parts (1.46 moles) of bis(2-hydroxyethyl) cocoamine (Ethomeen $C_{12}$), 219 parts (1.46 moles) of tartaric acid and 800 parts of toluene is prepared containing a few drops of titanium tetrabutoxide. The mixture is heated at the reflux temperature while removing water for a period of about 4 to 5 hours. Paratoluenesulfonic acid (1 part) is added to the mixture which is heated at reflux temperature while additional water is removed. The residue remaining in the reaction vessel is the desired product.

EXAMPLE 15-A

A mixture of 450 parts (3 moles) of tartaric acid, 432 parts of amino propyl morpholine and 500 parts of xylene is heated with stirring while removing water as an azeotrope. The remaining xylene is then removed from the reaction mixture. The residue is the desired product.

EXAMPLE 16-A

A mixture of 134 parts (1 equivalent) of malic acid, 524 parts (2 moles) of Adol 320, and about 2 parts of paratoluenesulfonic acid and 250 parts of toluene is prepared and heated with stirring to the reflux temperature. Water is removed as an azeotrope, thereafter toluene is removed and the reaction mixture is heated to about 180° C. Calcium hydroxide (0.8 part) is added, the reaction mixture is cooled and washed with water. The remaining toluene is removed and the residue is filtered through filter aid. The filtrate is the desired product.

EXAMPLE 17-A

A mixture of 948 parts (6 moles) of decyl alcohol and 500 parts of toluene is prepared, and 450 parts (3 moles) of tartaric acid and 2.47 parts of paratoluenesulfonic acid at the same time. The mixture is heated to the reflux temperature with nitrogen blowing, and water is removed. Toluene is then stripped from the reaction mixture at 19 mm Hg. and 100° C. The reaction mixture then is filtered through a filter aid and the filtrate is the desired product.

EXAMPLE 18-A

A mixture of 54 parts (0.6 mole) of lactic acid, 128 parts (0.60) of tridecyl alcohol, 250 parts of toluene and 0.95 part of paratoluenesulfonic acid is prepared and heated to the reflux temperature with nitrogen blowing. Water is removed followed by the addition of 0.4 part of calcium hydroxide while continuing to heat at the reflux temperature. Toluene is removed under partial vacuum and the reaction mixture is filtered through a filter aid. The filtrate is the desired product.

EXAMPLE 19-A

A mixture of 153 parts of DL tartaric acid hydrate, 400 parts of Procter & Gamble's CO-1214, one part of toluenesulfonic acid and 500 parts of toluene is heated to the reflux temperature of the mixture. Nitrogen is blown below the surface of the liquid and water is removed as the temperature reaches 190° C. A total of 35 parts of water are collected. The residue is filtered through a filter aid, and the filtrate is the desired product.

EXAMPLE 20-A

A mixture of 800 parts of the alcohol mixture of Example 19A, and 14 parts of water is heated to 50° C. whereupon sulfuric acid (107 parts) is added dropwise over a period of two hours and the temperature of the mixture reaches 60° C. Potassium bitartrate (376 parts) is added over ten minutes using high-speed stirring followed by heating to a temperature of about 94° C. for one hour. Xylene (500 ml) is added and the mixture is heated to reflux while collecting water. The temperature of the reaction mixture reaches 165° C. near the end of the esterification. 85 parts of water are collected. The residue is stripped at 140° C. and 30 mm Hg. This residue is filtered through a filter aid, and the filtrate is the desired product.

EXAMPLE 21-A

A mixture of 150 parts of tartaric acid, 288 parts of Alfol 810, 1.12 parts of paratoluenesulfonic acid and 400 parts of toluene is heated to reflux while collecting water in a sidearm trap. A total of 34 parts of water is collected. The mixture is stripped to 150° C./25 mm Hg. Calcium hydroxide (0.44 part) is added with stirring for 10 minutes at 80° C., and the mixture is filtered through a filter aid. The filtrate is the desired product.

EXAMPLE 22-A

A mixture of 75 parts of tartaric acid, 468 parts of Alfol 22+ S.P. and 1 part of paratoluenesulfonic acid is prepared and 400 parts of toluene is added. The mixture is heated to reflux for a total of 13 hours and a total of 16 parts of water is collected. The residue is stripped at 120° C./25 mm Hg. and filtered through a filter aid. The filtrate is the desired product having a saponification number of 96.3 (theory is 107).

EXAMPLE 23-A

A mixture of 199 parts of tartaric acid, 718 parts of commercial alcohol mixture available from Procter & Gamble under the general designation "CO1895F" containing about 2% $C_{16}$ and 96% $C_{18}$ fatty alcohols, and 1.1 part of paratoluenesulfonic acid is prepared and 500 parts of toluene is added. This mixture is heated to reflux for a total heating time of about 13 hours, and 47 parts of water is collected in a sidearm trap. The mixture is stripped at 135° C./25 mm Hg. The residue is filtered through a filter aid, and the filtrate is the desired product having a saponification number of 171 (theory is 172) and a melting point of 80°-81° C.

EXAMPLE 24-A

A mixture of 150 parts of tartaric acid, 590 parts of Aldol 158 (a commercial diol mixture available from Ashland Chemicals), 500 parts of toluene and 1.1 part of paratoluenesulfonic acid is heated to reflux while collecting 33 parts of water in a sidearm trap. The reaction mixture is stripped to 100° C./25 mm Hg., and the residue is filtered through a filter aid. The filtrate is the desired product having a saponification number of 168 (repeat 157; theory is 159).

EXAMPLE 25-A

A mixture of 150 parts of tartaric acid, 414 parts of Neodol 23 (a commercial mixture of $C_{12}$ and $C_{13}$ alcohols), 1 part of paratoluenesulfonic acid and 500 parts of toluene is prepared and heated to reflux. Water (36 parts) is collected in a sidearm trap. The mixture then is stripped at 135° C./27 mm Hg. and filtered through a filter aid. The filtrate is the desired product having a saponification number of 218 (theory is 212) and a melting point of 55°-56° C.

EXAMPLE 26-A

A mixture of 150 parts of tartaric acid, 436 parts of Neodol 45 (a commercial mixture of $C_{14}$ and $C_{15}$ alcohols), 1 part of paratoluenesulfonic acid and 500 parts of toluene is heated to reflux. Water (35 parts) is collected in a sidearm trap. The reaction mixture then is stripped at 110° C./21 mm Hg. and filtered through a filter aid. The filtrate is the desired product having a saponification number of 189 (theory is 204).

EXAMPLE 27-A

A mixture of 112.5 parts of tartaric acid, 480 parts of Adol 60 (a commercially available alcohol containing about 75% by weight of a straight chain $C_{22}$ primary alkanol, about 15% of a $C_{20}$ alcohol and about 8% of a mixture of $C_{18}$ and $C_{24}$ alcohols), 400 parts of toluene and 1 part of paratoluenesulfonic acid is heated to reflux. Water (25.5 parts) is collected in a sidearm trap. The mixture is stripped at 115° C./22 mm Hg. and filtered through a filter aid. The filtrate is the desired product having a saponification number of 139 (theory is 149).

EXAMPLE 28-A

A mixture of 150 parts of tartaric acid, 484 parts of an alcohol mixture available from Proctor & Gamble under the trade designation CO-1418 (comprising 1-4% $C_{12}$; 35-47% $C_{14}$; 15-27% $C_{16}$; and 30-40% $C_{18}$ alcohols), 400 parts of toluene and 2 parts of paratoluenesulfonic acid is prepared and heated to reflux while removing water through a sidearm trap. The mixture then is stripped to 122° C. at 16 mm Hg. The residue is filtered while hot through a filter aid, and the filtrate is the desired product.

EXAMPLE 29-A

Tartaric acid (150 parts) is added to 173 parts of toluene and the mixture is heated with stirring to 100° C. Armeen O (281 parts) is added slowly and in small portions while the system is kept under nitrogen purge. After the addition of the Armeen O is completed the contents are heated to 130° C. at which temperature the water formed is removed by azeotroping, and collected. The temperature is then raised to 160° C., after no more water is collected and kept at about 160° C. for one hour under nitrogen purge to remove the toluene. The liquid residue is then filtered through diatomaceous earth to yield the desired N-oleyltartarimide. Analysis shows nitrogen content of 3.42% and hydroxyl content of 8.33%.

EXAMPLE 30-A

Following the same procedure described in Example 29-A, 300 parts of tartaric acid are added to 519 parts of toluene and the mixture is heated with stirring to 90°-100° C. 370 parts of Armeen 12-D (distilled dodecylamine) are added slowly over about 2 hours. The temperature is raised to 110°-120° C. and the reaction is allowed to proceed for about 8 hours until no more water is observed. The reaction mixture is heated to 135° C. to strip the toluene (30 mm Hg.). The mixture is cooled and a portion of 2-ethyl hexanol is added and followed by filtering through diatomaceous earth to yield the desired N-dodecyl-tartarimide.

EXAMPLE 31-A

The same procedure and amounts described in Example 29-A is followed except the amine is substituted with 2-ethylhexylamine of which 258 parts are used. The reaction is conducted initially at 120° C. and then at 170° C. until all the water is removed (75 parts; theoretical 72 parts). The filtered solid is the desired product.

EXAMPLE 32-A

Tartaric acid (150 parts) is added to 173 parts of toluene and the mixture is heated with stirring to 110° C. Dodecylaniline (130 parts) is added to the heated mixture with nitrogen purge. The mixture including the amine is heated to 130° C. and held for about 5 hours. A second portion of the amine (130 parts) is added and the entire content is heated to 180° C. azeotroping out both the formed water and toluene. The tartarimide residue is allowed to cool to yield brown solid at room temperature.

The boron-containing compositions of the present invention are prepared by reacting (A) at least one of the above-identified hydroxy-substituted esters, amides or imides with (B) a boron compound selected from the group consisting of boric acid, boron trioxide, boron halides, boron amides and boron esters. Boron trioxide will react first with water which is present in the reaction mixture to form boric acid, which then reacts with reactant (A). Boric acid is the preferred boron compound, and any of the various forms of boric acid may be used, including metaboric acid ($HBO_2$) orthoboric acid ($H_3BO_3$) and tetraboric acid ($H_2B_4O_7$). The esters of these acids include, for example, the methyl, ethyl and propyl esters, with the methyl esters being most readily available and therefore the most often used.

The reaction between the hydroxy-substituted amide, imide or ester (reactor (A)) and boron compound (B) can be conducted at an elevated temperature up to but not including the decomposition temperature of any of the reactants or the product of the reaction. The decomposition point is that temperature (a+) which there is sufficient decomposition of any reactant or product such as to interfere with the production of the desired products. Generally the reaction between reactants (A) and (B) is conducted at a temperature within the range of from about 80° to about 200° C.

The amount of reactant (A) reacted with reactant (B) may be varied over a wide range and generally, the amounts are selected to provide a hydroxyl group to boron ratio in the mixture of from about 0.5:1 to about 4:1, and more generally, from about 1:1 to about 3:1. The reaction frequently is effective in the presence of a substantially inert, normally liquid organic diluent, typically an aromatic hydrocarbon such as toluene or xylene, a chlorinated aromatic hydrocarbon such as chlorobenzene, or an ether such as ethylene glycol dimethylether. Alternatively, reactants (A) and (B) can be reacted in the absence of added solvent.

The reaction of the hydroxy-substituted ester, amide or imide (reactant (A)) with the boron compound results in the formation of water which can be removed during the reaction, and the formation and removal of water provides a convenient method for determining when the reaction is completed. In some instances, all of the boron compound added to the reaction mixture does not react, and the unexpected boron compound remains as solid material which can be separated by filtration at the end of the reaction.

The following examples illustrate the preparation of the boron-containing compositions of the present invention.

EXAMPLE I A mixture of 387 parts (1.5 moles) of the product of Example 1-A, 46.35 parts (0.75 mole) of boric acid and 100 parts of toluene is prepared, heated to the reflux temperature and thereafter to a temperature of about 160° C. while removing water. The residue is filtered through a filter aid and the filtrate is stripped of volatile materials. The residue is the desired product containing 1.89% boron (theory, 1.99%).

EXAMPLE II

A mixture of 185 parts (0.8 mole) of the product of Example 2-A, 10.5 parts (0.17 mole) of boric acid and 300 parts of toluene is prepared with stirring and thereafter heated to the reflux temperature. Water is collected and after heating for about 5 hours, the mixture is allowed to cool overnight. The reaction product is then filtered and the filtrate is stripped to remove volatile materials. The residue is the desired product.

EXAMPLE III

The general procedure of Example II is repeated except that the mixture contains 15.4 parts (0.25 mole) of boric acid.

EXAMPLE IV

A mixture of 160 parts (0.43 mole) of the product of Example 2-A, 26.7 parts (0.43 mole) of boric acid and 200 parts of xylene is prepared and heated to the reflux temperature of xylene. Water is removed along with some xylene. Additional boric acid (26.7 parts, 0.43 mole) is then added, and a small amount of water is collected. Most of the second portion of boric acid is not incorporated into the product. The reaction mixture is filtered and the filtrate is stripped to remove water and xylene. The product obtained in this manner contains 3.04% boron indicating that slightly more than one mole of boric acid reacted with one mole of the product of Example 2-A.

EXAMPLE V

A mixture of 244 parts (1 mole) of the product of Example 3-A, 61 parts (1 mole) of boric acid, and 200 parts of toluene is prepared and heated to the reflux temperature. Water is collected, and thereafter toluene is removed. The reaction mixture is heated to a temperature of 150° C. and maintained at this temperature for about 3 hours. The amber viscous oil is filtered and stripped to remove volatile materials. The residue is the desired product containing 3.94% boron (theory, 4.01%).

EXAMPLE VI

A mixture of 245 parts (1 mole) of the product of Example 4-A and 62 parts (1 mole) of boric acid is prepared and heated to 140° C. while removing water. When most of the water is removed, the mixture is heated to 150° C. and maintained at this temperature until no more water can be collected. The reaction mixture is filtered to yield a dark amber syrup containing 3.77% boron (theory, 3.99%).

EXAMPLE VII

A mixture of 1645 parts (5 moles) of the product of Example 5-A, 154.5 parts (2.5 moles) of boric acid and 400 parts of toluene is prepared and heated to the reflux temperature while removing water. The residue is stripped to 160° C./25 mm Hg., filtered while hot through a filter aid, and the filtrate is the desired product containing 1.74% boron (theory, 1.58%).

EXAMPLE VIII

A mixture of 268 parts (1 mole) of the product of Example 6-A, 30.9 parts (0.5 mole) of boric acid and 100 parts of toluene is prepared and heated to the reflux temperature while removing water. The reaction mixture then is stripped to 120° C. at 25 mm Hg. The residue is the desired product containing 1.77% boron (theory, 1.92%).

EXAMPLE IX

A mixture of 384 parts (1 mole) of the product of Example 7-A, 30.9 parts (0.5 mole) of boric acid and 100 parts of toluene is heated to reflux while removing water under a nitrogen sweep. The reaction mixture then is stripped to 130° C./20 mm Hg., and the residue is the desired product containing 1.51% boron (theory, 1.30%).

EXAMPLE X

A mixture of 1010 parts (5 moles) of the product of Example 8-A and 387 parts (6.25 moles) of boric acid is prepared and heated to 160° C. with stirring. A strong nitrogen purge is used, and water is collected over a period of 12 hours. The reaction mixture then is filtered, and the filtrate is the desired product.

EXAMPLE XI

A mixture of 132 parts (0.35 mole) of the product of Example 10-A, 10.8 parts (0.17 mole) of boric acid and about 200 parts of toluene is heated to the reflux temperature, and water is removed. The reaction mixture is vacuum stripped to 140° C./20-40 mm Hg. The residue in the reaction vessel is the desired product containing 1.3% boron (theory, 1.3%).

EXAMPLE XII

A mixture of 342 parts (1 mole) of the product of Example 11-A, 30.9 parts (0.5 mole) of boric acid and 100 parts of toluene is heated to the reflux temperature with removal of water. The reaction mixture is stripped to 120° C./25 mm Hg., and the residue is the desired product containing 1.63% boron (theory, 1.52%).

EXAMPLE XIII

A mixture of 213 parts (0.3 mole) of the boron-containing product of Example XII, 102.6 parts (0.3 mole) of the product of Example 11-A and 100 parts of toluene is heated to reflux while removing water. The reaction mixture is stripped to 150° C./30 mm Hg., and the residue is the desired product containing 1.10% boron (theory, 1.04%).

EXAMPLE XIV

A mixture of 672 parts (2.75 moles) of the product of Example 3-A and 213 parts (3.43 moles) of boric acid is heated to 150° C. and water is removed. The residue is the desired product containing 4.85% boron (theory, 4.86%).

The boron-containing compositions of the invention can be effectively employed in a variety of lubricating compositions formulated for a variety of uses. The boron-containing compositions are useful particularly as friction-reducing and anti-wear agents. The use of the boron-containing compositions in lubricants results in improved fuel economy. These lubricating compositions are based on diverse oils of lubricating viscosity, including natural and synthetic lubricating oils and mixtures thereof. These lubricating compositions containing the subject additive are effective as crankcase lubricating oils for spark-ignited and compression-ignited internal combustion engines, including automobile and truck engines, two-cycle engines, aviation piston engines, marine and low-road diesel engines, and the like. Also, automatic transmission fluids, transaxle lubricants, gear lubricants, metal-working lubricants, hydraulic fluids, and other lubricating oil and grease compositions can benefit from the incorporation of the subject additive.

Natural oils include animal oils and vegetable oils (e.g., castor oil, lard oil) as well as mineral lubricating oils such as liquid petroleum oils and solvent-treated or acid-treated mineral lubricating oils of the paraffinic, naphthenic or mixed paraffinic-naphthenic types. Oils of lubricating viscosity derived from coal or shale are also useful. Synthetic lubricating oils include hydrocarbon oils and halosubstituted hydrocarbon oils such as polymerized and interpolymerized olefins (e.g., polybutylenes, polypropylenes, propylene-isobutylene copolymers, chlorinated polybutylenes, etc.); poly(1-hexenes), poly(1-octenes), poly(1-decenes), etc. and mixtures thereof, alkylbenzenes (e.g., dodecylbenzenes, tetradecylbenzenes, dinolylbenzenes, di-(2-ethylhexyl)-benzenes, etc.); polyphenyls (e.g., biphenyls, terphenyls, alkylated polyphenyls, etc.); alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc., constitute another class of known synthetic lubricating oils that can be used. These are exemplified by the oils prepared through polymerization of ethylene oxide or propylene oxide, the alkyl and aryl ethers of these polyoxyalkylene polymers (e.g., methylpolyisopropylene glycol ether having an average molecular weight of about 1000, diphenyl ether of polyethylene glycol having a molecular weight of about 500-1000, diethyl ether of polypropylene glycol having a molecular weight of about 1000-1500, etc.) or mono- and polycarboxylic esters thereof, for example, the acetic acid esters, mixed $C_3$-$C_8$ fatty acid esters, or the $C_{13}$Oxo acid diester of tetraethylene glycol.

Another suitable class of synthetic lubricating oils that can be used comprises the esters of dicarboxylic acids (e.g., phthalic acid, succinic acid, alkylsuccinic acids, alkenylsuccinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include those made from $C_5$ to $C_{12}$ monocarboxylic acids and polyols and polyol ethers such as neopentyl glycol, trimethylol propane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic lubricants (e.g., tetraethyl silicate, tetraisopropyl silicate, tetra-(2-ethylhexyl)silicate, tetra-(4-methylhexyl)silicate, tetra-(p-tert-butylphenyl)silicate, hexyl-(4-methyl-2-pentoxy)disiloxane, poly(methyl)siloxanes, poly(methylphenyl)siloxanes, etc.). Other synthetic lubricating oils include liquid esters of phosphorus-containing acids (e.g., tricresyl phosphate, trioctyl phosphate, diethyl ester of decane phosphonic acid, etc.), polymeric tetrahydrofurans and the like.

Unrefined, refined and rerefined oils, either natural or synthetic (as well as mixtures of two or more of any of these) of the type disclosed above can be used in the concentrates of the present invention. Unrefined oils are those obtained directly from a natural or synthetic source without further purification treatment. For example, a shale oil obtained directly from retorting operations, a petroleum oil obtained directly from primary distillation or ester oil obtained directly from an esterification process and used without further treatment would be an unrefined oil. Refined oils are similar to the unrefined oils except they have been further treated in one or more purification steps to improve one or more properties. Many such purification techniques are known to those skilled in the art such as solvent extraction, secondary distillation, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed to removal of spent additives and oil breakdown products.

Generally the lubricants of the present invention contain an amount of one or more of the compositions of this invention sufficient to provide them with improved friction-reducing, anti-wear and/or extreme pressure properties. Normally the amount employed will be about 0.01% to about 20%, preferably about 0.1% to about 10% of the total weight of the lubricating composition. This amount is exclusive of solvent/diluent medium. In lubricating compositions operated under extremely adverse conditions, such as lubricating compositions for marine diesel engines, the compositions of this invention may be present in amounts of up to about 30% by weight, or more, of the total weight of the lubricating composition.

The invention also contemplates the use of other additives in combination with the compositions of this invention. Such additives include, for example, detergents and dispersants of the ash-producing or ashless type, corrosion- and oxidation-inhibiting agents, pour point depressing agents, extreme pressure agents, antiwear agents, color stabilizers and anti-foam agents.

The ash-producing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature of about 50° C. and filtering the resulting mass. The use of a "promotor" in the neutralization step to aid the incorporation of a large excess of metal likewise is known. Examples of compounds useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-betanaphthylamine, and dodecylamine. A particularly effective method for preparing the basic salts comprises mixing an acid with an excess of a basic alkaline earth metal neutralizing agent and at least one alcohol promoter, and carbonating the mixture at an elevated temperature such as 60°–200° C.

Ashless detergents and dispersants are so called despite the fact that, depending on its constitution, the dispersant may upon combustion yield a nonvolatile material such as boric oxide or phosphorus pentoxide; however, it does not ordinarily contain metal and therefore does not yield a metal-containing ash on combustion. Many types are known in the art, and any of them are suitable for use in the lubricant compositions of this invention. The following are illustrative:

(1) Reaction products of carboxylic acids (or derivatives thereof) containing at least about 34 and preferably at least about 54 carbon atoms with nitrogen containing compounds such as amine, organic hydroxy compounds such as phenols and alcohols, and/or basic inorganic materials. Examples of these "carboxylic dispersants" are described in British Pat. No. 1,306,529 and in many U.S. Patents including the following:

U.S. Pat. Nos. 3,163,603, 3,351,552, 3,541,012, 3,184,474, 3,381,022, 3,543,678, 3,215,707, 3,399,141, 3,542,680, 3,219,666, 3,415,750, 3,567,637, 3,271,310, 3,433,744, 3,574,101, 3,272,746, 3,444,170, 3,576,743, 3,281,357, 3,448,048, 3,630,904, 3,306,908, 3,448,049, 3,632,510, 3,311,558, 3,451,933, 3,632,511, 3,316,177, 3,454,607, 3,697,428, 3,340,281, 3,467,668, 3,725,441, 3,341,542, 3,501,405, 4,234,435, 3,346,493, 3,522,179, Re 26,433.

(2) Reaction products of relatively high molecular weight aliphatic or alicyclic halides with amines, preferably olyalkylene polyamines. These may be characterized as "amine dispersants" and examples thereof are described for example, in the following U.S. Pat. Nos. 3,275,554, 3,454,555, 3,438,757, 3,565,804.

(3) Reaction products of alkyl phenols in which the alkyl group contains at least about 30 carbon atoms with aldehydes (especially formaldehyde) and amines (especially polyalkylene polyamines), which may be characterized as "Mannich dispersants". The materials described in the following U.S. Patents are illustrative:

U.S. Pat. Nos. 2,459,112, 3,442,808, 3,591,598, 2,962,442, 3,448,047, 3,600,372, 2,984,550, 3,454,497, 3,634,515, 3,036,003, 3,459,661, 3,649,229, 3,166,516, 3,461,172, 3,697,574, 3,236,770, 3,493,520, 3,725,277, 3,355,270, 3,539,633, 3,725,480, 3,368,972, 3,558,743, 3,726,882, 3,413,347, 3,586,629, 3,980,569.

(4) Products obtained by post-treating the carboxylic, amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. Patents:

U.S. Pat. Nos. 3,036,003, 3,282,955, 3,493,520, 3,639,242, 3,087,936, 3,312,619, 3,502,677, 3,649,229, 3,200,107, 3,366,569, 3,513,093, 3,649,659, 3,216,936, 3,367,943, 3,533,945, 3,658,836, 3,254,025, 3,373,111, 3,539,633, 3,697,574, 3,256,185, 3,403,102, 3,573,010, 3,702,757, 3,278,550, 3,442,808, 3,579,450, 3,703,536, 3,280,234, 3,455,831, 3,591,598; 3,704,308, 3,281,428; 3,455,832, 3,600,372; 3,708,422.

These concentrates usually contain from about 10% to about 90% by weight of the boron-containing compositions of this invention and may contain, in addition, one or more other additives known in the art or described hereinabove. The remainder of the concentrate is the substantially inert normally liquid diluent.

The boron-containing compositions of the invention are useful particularly for improving the anti-wear properties of lubricants containing little or no phosphorus, especially lubricants containing less than 0.1% phosphorus especially as a phosphorodithioate. In such low phosphorus lubricants, it is preferred to use a boron-containing composition derived from a hydroxy-containing ester.

The boron-containing compositions of the invention also are useful as fuel additives. The fuel compositions of the present invention contain a major proportion of a normally liquid fuel, usually a hydrocarbonaceous petroleum distillate fuel such as motor gasoline as defined by ASTM Specification D439 and diesel fuel or fuel oil as defined by ASTM Specification D396. Normally liquid fuel compositions comprising nonhydrocarbonaceous materials such as alcohols, ethers, organo-nitro compounds and the like (e.g., methanol, ethanol, diethyl ether, methyl ethyl ether, nitromethane) are also within the scope of this invention as are liquid fuels derived from vegetable or mineral sources such as corn, alfalfa, shale and coal. Normally liquid fuels which are mixtures of one or more hydrocarbonaceous fuels and one or more non-hydrocarbonaceous materials are also contemplated. Examples of such mixtures are combinations of gasoline and ethanol and of diesel fuel and ether. Particularly preferred is gasoline, that is, a mixture of hydrocarbons having an ASTM distillation range from about 60° C. at the 10% distillation point to about 205° C. at the 90% distillation point.

Generally, these fuel compositions contain a property improving amount of the boron-containing compositions of this invention; usually this amount is about 1 to about 50,000 parts by weight, preferably about 4 to about 5000 parts, of the composition of this invention per million parts of fuel.

The fuel compositions can contain, in addition to the boron-containing composition of this invention, other additives which are well known to those of skill in the art. These include antiknock agents such as tetraalkyl lead compounds, lead scavengers such as haloalkanes (e.g., ethylene dichloride and ethylene dibromide), deposit preventers or modifiers such as triaryl phosphates, dyes, cetane improvers, antioxidants such as 2,6-ditertiary-butyl-4-methyl-phenol, rust inhibitors such as alkylated succinic acids and anhydrides, bacteriostatic agents, gum inhibitors, metal deactivators, demulsifiers, upper cylinder lubricants and anti-icing agents.

In certain preferred fuel compositions the boron compositions of this invention are combined with an ashless dispersant in gasoline. Suitable ashless dispersants include esters of mono- or polyols and high molecular weight mono- or polycarboxylic acid acylating agents containing at least 30 carbon atoms in the acyl moeity. Such esters as well known to those skilled in the art. See, for example, French Pat. No. 1,396,645; British Pat. Nos. 981,850; 1,055,337 and 1,306,529; and U.S. Pat. Nos. 3,255,108; 3,311,558; 3,331,776; 3,346,354; 3,522,179; 3,579,450; 3,542,680; 3,381,022; 3,639,242; 3,697,428; and 3,708,522. These patents are expressly incorporated herein by reference for their disclosure of suitable esters and methods for their preparation. Generally, the weight ratio of the composition of this invention to the aforesaid ashless dispersant is between about 0.1:1 and about 10:1, preferably between about 1:1 and about 10:1.

The boron-containing compositions of this invention can be added directly to the fuel, or they can be diluted with a substantially inert, normally liquid organic diluent such as naphtha, benzene, toluene, xylene or a normally liquid fuel as described above, to form an additive concentrate. These concentrates generally contain from about 10% to about 90% by weight of the composition of this invention and may contain, in addition one or more other conventional additives known in the art or described hereinabove.

We claim:

1. A method of preparing a boron-containing composition which comprises reacting
(A) a hydroxy-substituted amide of the formula

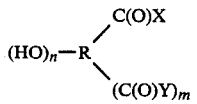  (I)

wherein R is a divalent hydrocarbyl group, X is —NR'R", wherein R' is a hydrocarbyl group and R" is hydrogen or a hydrocarbyl group, Y is OH or X, m is 1 or 2, and n is an integer from 1 to 10 provided that only one free hydroxyl group is attached per carbon atom of the hydrocarbyl group R; with
(B) a boron compound selected from the group consisting of boric acid, boron trioxide, boron halides, boron amides and boron esters and wherein (A) is reacted with (B) at an elevated temperature up to but not including the decomposition temperature of any reactants or the product of the reaction and wherein the ratio of the hydroxyl group to the boron compound is from about 0.5:1 to about 4:1.

2. The method of claim 1 wherein (A) is a hydroxy-substituted amide having the structure $$(HO)_n-R-(C(O)NR'R'')_m \quad (II)$$

wherein m, n, R, R' and R" are as defined in claim 1.

3. The method of claim 2 wherein (A) is represented by Formula II and R" is hydrogen.

4. The method of claim 1 wherein R' and R" are each independently hydrocarbyl groups containing from 4 to about 30 carbon atoms.

5. The method of claim 3 wherein R' contains from about 4 to about 30 carbon atoms.

6. The method of claim 2 wherein the hydrocarbyl group R' is an aliphatic hydrocarbyl group.

7. The method of claim 1 wherein the hydrocarbyl group R is an alkylene, alkenylene, alkynylene, arylene or alkarylene group containing from 1 to about 10 carbon atoms.

8. The method of claim 7 wherein the hydrocarbyl group R is an alkylene group containing from 1 to about 6 carbon atoms and n is from 1 to 6.

9. The method of claim 2 wherein R contains from 1 to 3 carbon atoms, n is 1 to 3.

10. The method of claim 1 wherein (B) is boric acid.

11. The method of claim 2 wherein (B) is boric acid.

12. The method of claim 1 wherein the reaction is conducted at a temperature within the range of from about 80° to about 200° C.

13. The method of claim 2 wherein the hydroxy-substituted amide (A) is prepared by the reaction of
(A-1) a hydroxy-substituted carboxylic acid, ester or halide of the formulae $$(HO)_nRC(O)Y', \text{ or} \quad (V)$$

  (VI)

or the anhydrides of said acids, wherein Y' is —OH, a halogen, or OR''' wherein R''' is a lower alkyl group, or a lactone of the formula

  (VII)

with
(A-2) at least one primary or secondary hydrocarbyl amine of the general formula $$R'R''NH \quad (VIII)$$

wherein m, n, R, R' and R" are as defined in claim 2.

14. The method of claim 13 wherein (A-1) is a hydroxy-substituted carboxylic acid.

15. The method of claim 13 wherein (A-1) is represented by Formula V, and R contains from 1 to about 6 carbon atoms, n is an integer from 1 to about 5, and R" is hydrogen.

16. The method of claim 13 wherein (A-1) is represented by Formula VI and R contains from 1 to 3 carbon atoms.

17. The method of claim 13 wherein n is 1 or 2.

18. The method of claim 13 wherein (A-1) and (A-2) are heated at an elevated temperature up to about the decomposition point of the reactants or the product mixture.

19. The method of claim 13 wherein about equivalent amounts of (A-1) and (A-2) are reacted.

20. A method of preparing boron-containing compositions which comprises reacting
(A) an amide of a hydroxy-substituted carboxylic having the formula $$(HO)_n-R-(C(O)NR'R'')_m \quad (II)$$

wherein R is a divalent aliphatic group containing from one to 6 carbon atoms, R' is an aliphatic group containing from about six to about 30 carbon atoms, R'' is hydrogen or an R' group, m is 1 or 2, n is an integer from 1 to about 5; with
(B) a boron compound selected from the group consisting of boric acid, boron oxide, boron halides, boron amides and boron esters in a ratio of hydroxyl group to born of from about 0.5:1 to about 3:1 and wherein (A) is reacted with (B) at an elevated temperature up to but not including the decomposition temperature of any reactants or products thereof.

21. The process of claim 20 wherein the reaction is conducted at a temperature of from about 80° C. to about 200° C.

22. The process of claim 20 wherein the ratio of hydroxyl groups to boron is about 1:1 to about 3:1.

23. The process of claim 20 wherein (B) is boric acid.

24. The process of claim 20 wherein (A) is derived from the reaction of
(A-1) a hydroxy-substituted carboxylic acid, ester or acid halide $$(HO)_nRC(O)Y', \text{ or} \quad (V)$$

or the anhydride of said acids wherein Y' is —OH, a halogen, or OR''' wherein R''' is a lower alkyl group, or a lactone of the formula

with
(A-2) at least one primary or secondary hydrocarbyl amine of the general formula $$R'R''NH \quad (VIII)$$

wherein m, n, R, R' and R'' are as defined in claim 20.

25. The process of claim 24 wherein (A-1) is a hydroxy-substituted carboxylic acid.

26. The process of claim 24 wherein R'' is hydrogen.

27. The process of claim 20 wherein (A) is an amide of hydroxyacetic acid or lactic acid (B) is boric acid.

28. A boron-containing composition prepared by the process of claim 1.

29. A boron-containing composition prepared in accordance with the process of claim 20.

30. A boron-containing composition prepared in accordance with the process of claim 27.

31. An additive concentrate comprising a substantially inert, normally liquid organic solvent/diluent and about 10-90% by weight of a composition accoding to claim 28.

32. An additive concentrate comprising a substantially inert, normally liquid organic solvent/diluent and about 10-90% by weight of a composition according to claim 29.

33. A lubricating composition comprising a major amount of a lubricating oil and a minor amount of at least one composition of claim 28.

34. A lubricating composition comprising a major amount of a lubricating oil and a minor amount of at least one composition of claim 29.

* * * * *